US009335156B2

(12) United States Patent
Campagne et al.

(10) Patent No.: US 9,335,156 B2
(45) Date of Patent: May 10, 2016

(54) METHOD AND DEVICE FOR TESTING A COMPOSITE MATERIAL USING LASER ULTRASONICS

(71) Applicant: Airbus Operations (S.A.S.), Toulouse (FR)

(72) Inventors: Benjamin Campagne, Saint Herblain (FR); Franck Bentouhami, Chavannes en Paillers (FR)

(73) Assignee: AIRBUS OPERATIONS (S.A.S.), Toulouse (FR)

( * ) Notice: Subject to any disclaimer, the term of this patent is extended or adjusted under 35 U.S.C. 154(b) by 0 days.

(21) Appl. No.: 14/491,767

(22) Filed: Sep. 19, 2014

(65) Prior Publication Data

US 2015/0109611 A1    Apr. 23, 2015

Related U.S. Application Data

(63) Continuation of application No. PCT/EP2013/055504, filed on Mar. 18, 2013.

(30) Foreign Application Priority Data

Mar. 20, 2012 (FR) ...................................... 12 52492

(51) Int. Cl.
*G01N 21/00* (2006.01)
*G01B 9/02* (2006.01)
(Continued)

(52) U.S. Cl.
CPC ............ *G01B 9/02091* (2013.01); *G01B 11/06* (2013.01); *G01N 21/1702* (2013.01); *G01N 29/069* (2013.01); *G01N 29/225* (2013.01); *G01N 29/2418* (2013.01); *G01B 11/0675* (2013.01); *G01N 2201/06113* (2013.01);
(Continued)

(58) Field of Classification Search
CPC ............ G01N 29/069; G01N 29/2418; G01N 2291/0231; G01N 2291/2694; B23K 26/38; G01B 11/0675; G01B 9/02091
See application file for complete search history.

(56) References Cited

U.S. PATENT DOCUMENTS 6,130,402 A * 10/2000 Abella et al. ............. 219/121.68
6,496,268 B1 * 12/2002 McKie et al. ................. 356/503
(Continued)

OTHER PUBLICATIONS

International Search Report for Application No. PCT/EP2013/055504 dated Apr. 5, 2013.
(Continued)

*Primary Examiner* — Michael A Lyons
*Assistant Examiner* — Maurice Smith
(74) *Attorney, Agent, or Firm* — Jenkins, Wilson, Taylor & Hunt, P.A.

(57) ABSTRACT

This disclosure relates to a method for the nondestructive testing, using laser ultrasonics, of a composite part having a fibrous reinforcement in a resin that optically scatters the laser, includes: a) taking a measurement of the thickness of the resin of the part on the surface that is illuminated during the laser shot, which is capable of generating a thermoelastic effect in said resin and which is referred to as an ultrasonic laser shot; b) adjusting the power of the laser of said ultrasonic shot on the basis of the thickness measurement carried out in step a) so as to eliminate any risk of a flash on the reinforcements; and c) producing the ultrasonic laser shot at the power determined during step b). The device used for implementing the method comprises a combined photoacoustic imaging and low time-coherence interferometry (OCT) system.

10 Claims, 3 Drawing Sheets

(51) Int. Cl.
| | |
|---|---|
| *G01N 29/06* | (2006.01) |
| *G01N 29/22* | (2006.01) |
| *G01N 29/24* | (2006.01) |
| *G01N 21/17* | (2006.01) |
| *G01B 11/06* | (2006.01) |

(52) U.S. Cl.
CPC .... *G01N2201/08* (2013.01); *G01N 2291/0231* (2013.01); *G01N 2291/2694* (2013.01)

(56) References Cited

U.S. PATENT DOCUMENTS

| | | | | |
|---|---|---|---|---|
| 6,543,288 | B1* | 4/2003 | Blouin et al. | 73/643 |
| 2003/0000927 | A1* | 1/2003 | Kanaya et al. | 219/121.7 |
| 2003/0020922 | A1* | 1/2003 | Crowley et al. | 356/502 |
| 2003/0227614 | A1* | 12/2003 | Taminiau et al. | 356/125 |
| 2004/0054357 | A1* | 3/2004 | O'Donnell | 606/4 |
| 2005/0211680 | A1* | 9/2005 | Li et al. | 219/121.68 |
| 2007/0013917 | A1* | 1/2007 | Stubbe et al. | 356/511 |
| 2007/0181543 | A1* | 8/2007 | Urairi et al. | 219/121.71 |
| 2008/0079949 | A1* | 4/2008 | Kuroiwa | 356/496 |
| 2010/0249562 | A1* | 9/2010 | Zhang et al. | 600/365 |
| 2011/0080591 | A1* | 4/2011 | Johnson et al. | 356/479 |
| 2011/0284508 | A1* | 11/2011 | Miura et al. | 219/121.64 |

OTHER PUBLICATIONS

McKie A D W et al: " Practical considerations for the rapid inspection of composite materials using laser-based ultrasound", Ultrasonics, IPC Science and Technology Press Ltd. Guildford, GB, vol. 32, No. 5, Sep. 1, 1994, pp. 333-345, XP025703959, ISSN: 0041-624X, DOI:10.1016/0041-624X(94)90103-1 [extra it le Sep. 1, 1994] abrégége p. 336, colonne de gauche, alinéa 3 -colonne de droite, alinéa 1 page 343, colonne de gauche, alinéa 2 figures 6, 16.

Shuliang Jiao et al: "Simultaneous multimodal imaging with integrated photoacoustic microscopy and optical coherence tomography", Optics Letters, OSA, Optical Society of America, Washington, DC, US, vol. 34, No. 19, Oct. 1, 2009, pp. 2961-2963, XP001548597, ISSN: 0146-9592, DOI: 10.1364/0L.34.002961 [extrait le Sep. 24, 2009] abrégé p. 2961, colonne de droite, alinéa 3—p. 2962, colonne de gauche, alinéa 4 figures 1-3.

Edwards C et al: "Laser generated ultrasound: efficiency and damage thresholds in carbon fibre reinforced composites". IEE Proceedings: Science, Measurement and Technology, IEE, Stevenage, Herts, GB, vol. 148, No. 4, Jul. 3, 2001, pp. 139-142, XP006017097, ISSN: 1350-2344, DOI: 10.1049/IP-SMT:20010465 abrégé Section 3.1 figure 3.

M Dubois et al: "Optimization of temporal profile and optical penetration depth for laser-generation of ultrasound in polymer-matrix composites", Review of Progress in Uantitative Nondestructive Evaluation, vol. 19, Jul. 25, 1999, pp. 287-294, XP055040206, DOI: 10.1063/1.1306063 pp. 292, alinéa 1-p. 293, aliné figures 2,9,10.

* cited by examiner

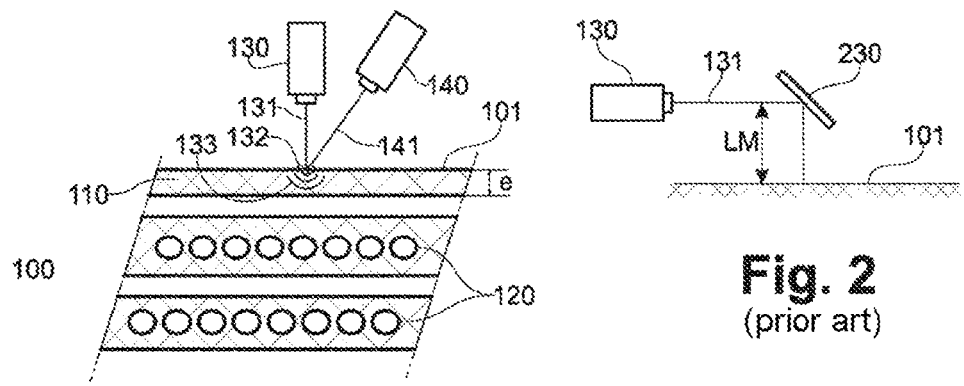
Fig. 1
(prior art)
Fig. 2
(prior art)
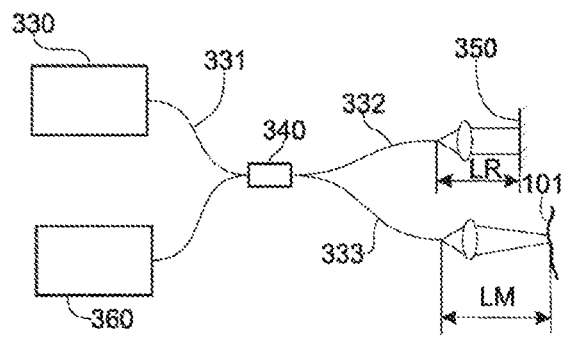
Fig. 3
(prior art)
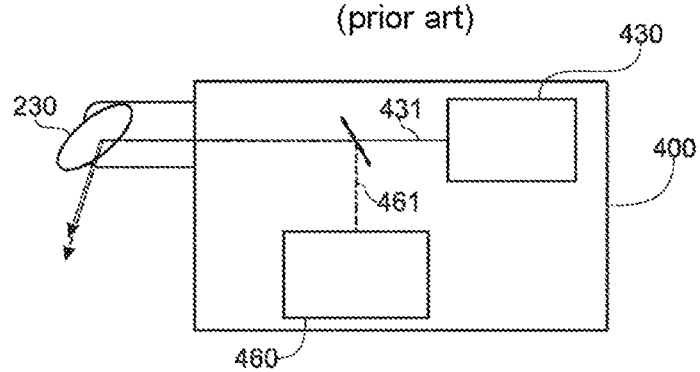
Fig. 4

METHOD AND DEVICE FOR TESTING A COMPOSITE MATERIAL USING LASER ULTRASONICS

CROSS-REFERENCE TO RELATED APPLICATIONS

This application is a continuation of PCT Patent Application No. PCT/EP2013/055504 filed Mar. 18, 2013 which claims the benefit of and priority to French Patent Application No. FR 12 52492, filed Mar. 20, 2012, the entire disclosures of which are incorporated by reference herein.

TECHNICAL FIELD

The disclosure herein relates to a method and device for testing a composite material using laser ultrasonics. The disclosure herein is more particularly related to non-destructive testing of parts made of a composite material containing reinforcing fibers, the nature of the fibers being such that absorption of the energy of the laser beam over a large thickness is unviable as the fibers, carbon fibers or metal fibers for example, thus excited, are liable to produce flashes.

BACKGROUND

Nondestructive ultrasonic testing of the material health of composite materials is known from the prior art. Such methods are advantageously implemented by ultrasound generated by a thermoelastic excitation of the surface of the parts made from these materials, created by localized and rapid heating of the surface with a laser beam, an energy comprised between 1 and 5 joules·cm$^{-2}$ being deposited on the surface. The composite materials of concern by the method of the disclosure are made up of reinforcing fibers in a thermoplastic or thermosetting organic matrix such as an epoxy resin. It is this resin that absorbs the laser radiation and the response of which to this excitation produces thermoelastic effect that gives rise to the ultrasonic mechanical wave, the analysis of the propagation of this wave in the material allowing the nondestructive test to be carried out. In order for this effect to be possible, the light energy deposited on the surface must be absorbed by a sufficient volume of resin in order for the light energy to be converted into mechanical energy before the laser beam reaches the reinforcements. Specifically, if the reinforcements are touched by the light wave, they produce flashes, thereby degrading the reinforcement and possibly even vaporizing the surrounding resin.

Thus, the amount of energy deposited on the surface of the part by each shot must be adjusted depending on the thickness of resin separating the first reinforcements from the surface of the part.

In the prior art, the excitation power of the laser generating the ultrasonic wave is adjusted on a control sample of the material making up the part to be tested or on a representative zone of the part. The parameters of the laser shots are then adjusted by visual inspection and based on the experience of the operator, and are kept constant for the inspection of the entire part. Nevertheless, more particularly for large parts, the external resin layer of the latter may contain thickness variations or may even be missing in places. Under these conditions, flashes of light are liable to be generated during the testing of the part even though the parameters of this test were adjusted beforehand on a sample.

SUMMARY

The disclosure herein aims to solve the drawbacks of the prior art and relates, for this purpose, to a method for nondestructive laser ultrasonic testing of a composite part containing a fibrous reinforcement in a resin that optically scatters the laser light, the method comprising:

a) measuring the thickness of the resin of the part in the area that is illuminated when a laser shot is fired, this laser shot, called a laser ultrasonic shot, being able to generate a thermoelastic effect in the resin;

b) adjusting the power of the laser of the ultrasonic shot depending on the thickness measurement carried out in step a) so as to prevent any risk of the reinforcements producing flashes; and c) firing the laser ultrasonic shot at the power determined in step b).

Thus, the power of the laser ultrasonic shot is adjusted or the laser ultrasonic shot is even cancelled in certain zones in order to inhibit any flash effects in the reinforcements.

The disclosure may be implemented according to the advantageous embodiments described below, which may be considered individually or in any technically workable combination.

Advantageously, the thickness measurement in step a) is achieved by an optical coherence tomography (abbreviated OCT) technique. Thus, the thickness measurement is also carried out by laser radiation and may share structure, especially the scanner, with the laser ultrasonic shot device, guaranteeing that the position of the thickness measurement on the part and the position of the laser shot are coincident.

According to a first variant of the method of the disclosure, step b) is carried out by modifying the focus of the laser of the ultrasonic shot.

According to a second variant of the method of the disclosure, step b) is carried out by modifying the power of the laser radiation of the ultrasonic shot.

These two variants may be combined or selected depending on the energy level required given the resin thickness.

According to a first embodiment, step a) of the method of the disclosure comprises:

ai) taking a series of thickness measurements over the entire area of the part; and aii) recording the thickness values thus measured in a table containing for each thickness value a spatial location of the measurement point.

Thus, a map of surface resin thicknesses may be produced for the part before the ultrasonic testing. This thickness map is also a nondestructive test of the part since regions poor in or even devoid of resin also form material health flaws.

According to a second embodiment of the method of the disclosure, steps a) to c) are carried out in succession for each laser ultrasonic shot.

Thus, the surface resin thickness measurement and the ultrasonic testing are carried out in one and the same test operation.

The disclosure also relates to a device for implementing the method of the disclosure, which device comprises:

i) a laser source able to produce laser ultrasonic shots;

ii) a device, called an OCT device, comprising a laser source and an interferometer detector;

iii) an optical path, referred to as the measurement leg, of length LM comprising a scanning mirror, able to project onto the part the laser radiation from the ultrasonic source and the OCT laser radiation;

iv) an optical path, referred to as the reference leg, separate from the measurement optical path, and comprising an optical fiber of length Lf and a mirror, called the reference mirror, placed at a distance Lz from the exit of the optical fiber such that LM=Lf+Lz; and v) a firing rate control for controlling the firing rate of the laser ultrasonic shots and the shots of the OCT laser source so that such shots are separated by a time Δt.

The OCT (optical coherence tomography) method is suitable for measuring the thickness of transparent or scattering media such as the resin of the part. Thus, the device of the disclosure allows two types of measurement, sharing implementation structure, to be combined and the power of the laser ultrasonic shots to be adapted depending on the resin thickness at the exact point of the part at which the shot is fired. Using an optical path, called the reference path, comprising an optical fiber, allows, by way of the length of the optical fiber, the same scanning mirror distance, relative to the part, to be preserved for both the OCT measurement and the laser ultrasonic shot.

Advantageously, the device of the disclosure comprises:

vi) a motorized displacement stage holding the reference mirror so that the distance Lz may be varied.

Thus, the length of the reference leg may be adapted, especially in order to take into account the shape of the part, by moving the reference mirror.

Advantageously, the device of the disclosure furthermore comprises:

vii) calculating and control structure configured to determine the thickness of the resin detected by the OCT shot and to adjust the focus or the power of the laser ultrasonic shot in a time shorter than or equal to Δt.

Thus, the adjustment of the power of the laser ultrasonic shot is tailored to and carried out automatically for each shot.

Advantageously, Δt is shorter than or equal to 10 ms. Thus, as seen by the operator, the power of the laser ultrasonic shot is adjusted in real time, and, compared to the prior art, introduction of the additional thickness measurement does not decrease the productivity of the nondestructive test procedure.

BRIEF DESCRIPTION OF THE DRAWINGS

Preferred but completely nonlimiting embodiments of the disclosure are described below with reference to FIGS. 1 to 9, in which:

FIG. 1, relating to the prior art, illustrating, via a partial cross-sectional front view, the principle of laser ultrasonic measurement of a composite part containing fibrous reinforcements;

FIG. 2, relating to the prior art, shows, via a front view, an example optical path of a laser for illuminating the surface of a part, the optical path comprising a scanning mirror;

FIG. 3, relating to the prior art, schematically illustrating an OCT device;

FIG. 4 is a schematic cross-sectional profile view of a measurement head according to one embodiment of the device of the disclosure, which measurement head contains a scanning mirror;

DETAILED DESCRIPTION

Figure 5:
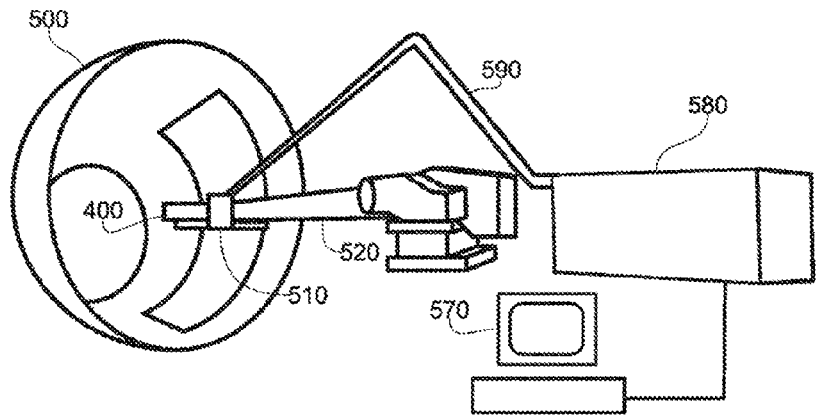
FIG. 5 illustrates, via a perspective view, a device for testing a large aerospace part according to one embodiment of the device of the disclosure.

Referring for example to FIG. 1, laser ultrasonic testing of a composite part (100) containing a fibrous reinforcement (120) in an organic matrix (110) formed from a thermosetting or thermoplastic resin, is achieved by an excitation laser beam (131). A localized excitation (132) is produced on the surface (101) of the part by a thermoelastic effect exposing a small area of the part to the energy, delivered in pulse form, of a laser ray (131), or shot, which ray is produced by a suitable source (130). Typically, the laser source used is a TEA (transversely excited atmospheric pressure) $CO_2$ laser, i.e. a laser obtained by excitation of carbon dioxide at atmospheric pressure. This thermoelastic disturbance of the surface (101) produces a mechanical wave (133) that propagates elastically, at the speed of sound in the medium forming the part. Discontinuities in the medium modify the propagation conditions of the mechanical wave (133), a second laser ray (141), called the detection ray, of lower power, and generated by a source (140) of a different nature, for example an Nd:YAG laser, allows, by interferometry, the deformation of the surface (101) of the part to be measured, by interference of this detection laser with a so-called reference beam in an interferometer. This measurement makes it possible to determine the propagation conditions of the mechanical wave, especially its reflections from discontinuities in the medium, and thus to detect such discontinuities, especially flaws. The principle of laser ultrasonic testing is known from the prior art and is not described in greater detail below.

FIG. 2, according to one common embodiment, the laser beams follow an optical path and are projected onto the surface (101) of the part by a device comprising a motorized scanning mirror (230) allowing a focal distance LM of the ray (141) to be adjusted and the ray to be moved over the surface of the part without moving the source (130).

Returning to FIG. 1, the conditions for obtaining the creation of a purely thermoelastic effect during the excitation of the surface (101) depend on the nature of the excited material, and these conditions: wavelength and power of the laser, pulse length, size of the excited zone, are modified depending on the nature of the medium. In the case of a composite comprising an organic matrix, the resin forming the matrix is a scattering medium but generally is more transparent than the reinforcements, which may have optical, mechanical and thermal properties that are very different from those of the matrix. Thus, thermoelastic effect is created in the surface thickness, e, so that most of the power of the incident excitation laser beam (141) is dissipated before the ray reaches the reinforcements (120). In the contrary case, depending on the nature of the reinforcements, especially when the latter are made from carbon, aramide or metal fibers, the latter are not able to scatter the beam in their thickness, and, when the laser beam reaches them, a flash is produced that precedes a regime of ablative interaction of the laser with the fibers. Thus, the reinforcement is degraded locally and these effects may even lead to the surrounding resin vaporizing, so that the effect may possibly be amplified by the following shot.

FIG. 3, the OCT measurement method uses a low coherence light source (330). The illuminating beam is focused on the surface of the sample analyzed. Photons backscattered by the sample interfere with a reference beam, the reference beam being obtained by splitting the beam (331) of the light source in a beam splitter (340), one half (333) of this beam is directed toward the surface (101) of the sample to be analyzed, thereby forming a measurement leg, of length LM, and the other half (332) of the beam is directed toward a reference mirror (360), forming a reference leg of length LR. The measurement leg and the reference leg are of equal length. A spectrometer detector (360) makes it possible to generate a signal quantifying the interference of the beams and to deduce therefrom properties of the sample, especially its thickness. In the prior art, LM is between 10 and 30 mm.

Referring for example to FIG. 4, the device of the disclosure uses, according to one embodiment, an OCT measurement module (460) and a laser ultrasonic testing module (430) located in one and the same measurement head (400). The two modules use different laser beams (431, 461) but share the same scanner (230).

FIG. 5, according to one embodiment, the device of the disclosure is suitable for nondestructive testing of large parts, especially of parts (500) making up the structure of an aircraft. According to this embodiment, an effector-carrier (510) receives the measurement head (400). According to this embodiment of the device of the disclosure, the effector-carrier (510) is supported by a robotic arm (520) that allows the measurement head (400) to be moved from one zone to another, the scanning of the surface of the part inside a given zone being achieved by moving the scanning mirror contained in the measurement head (400). An information-processing device (570) allows the movement of the robotic arm to be controlled, by digital control, and the processing and acquisition of the measurements to be carried out. The TEA $CO_2$ laser intended to generate the ultrasonic shots is produced by a stationary generator (580) and transmitted to the measurement head (400) by a hinged waveguide device (590). Typically, the scanning mirror is located at a distance comprised between 300 mm and 2 m from the surface of the part, in order to prevent any collision with the latter, and this distance is liable to vary in a range of at least 500 mm from one measurement zone to another on account of the shape of the part (500). This distance between the scanning mirror and the surface of the part is similar to the length LM of the measurement leg. Thus, regarding the OCT module, the need for a reference leg of equal length to the measurement leg poses a technical problem of compactness, with respect to integration of the module into the measurement head, and also creates a problem with adjustment of the reference arm to take variations of the length LM into account.

Figure 6:
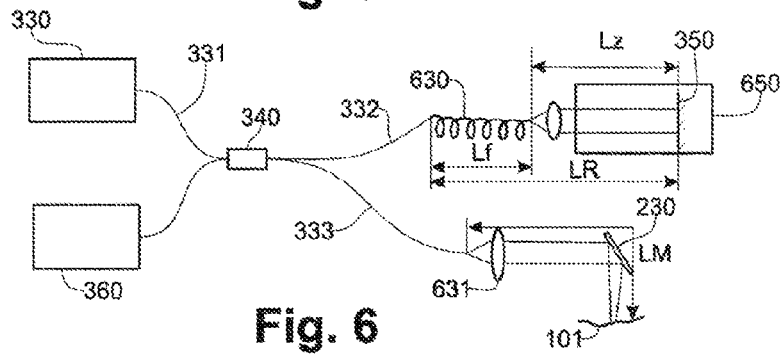
FIG. 6 schematically illustrates the OCT module according to one embodiment of the device of the disclosure.

FIG. 6, the OCT module integrated into the measurement head of the device of the disclosure comprises an optical fiber (630) of optical length Lf, on the optical path forming the reference leg. The optical length depends on the refractive index of the optical fiber. Thus, the length of the reference leg may be equivalent to that of the measurement leg without the bulk of the measurement head being increased in the same proportions. The reference mirror (350) is movably mounted translationally on a carriage (650) so that the distance, Lz, between the exit of the optical fiber (630) and the reference mirror may be controlled. The length LR of the reference leg is the sum LR=Lf+Lz.

The optical path corresponding to the measurement leg, of length LM, illuminating the surface of the part (101) via a scanning mirror (230), comprises a focusing lens (631) allowing an optical spot smaller than a given diameter to be obtained at the distance LM from the lens (631), the diameter depending on the targeted application. The diameter, D, of the focusing lens (631) depends on the diameter, D', of the optical spot targeted on the surface of the part (101), on the focal length, f, and on the wavelength $\lambda$ of the laser radiation used, as defined by the relationship $D'=4\lambda f/\pi D$. In the completely nonlimiting example of the application of the device of the disclosure to the testing of large aerospace parts, the targeted diameter D is smaller than or equal to 500 µm ($500 \times 10^{-6}$ m). In practice, the distance between the lens (631) and the scanning memory (230) is constant and very small relative to the distance between the scanning mirror (230) and the surface of the part (101).

The optical interferometry principle used for the OCT requires the lengths LM and LR to remain equal to within a tolerance that depends on the targeted application. In the completely nonlimiting example of application of the device of the disclosure to the testing of large aerospace parts, this tolerance is 500 µm. Thus, the translational device (650) of the reference mirror (350) allows, on the one hand, the length LR of the reference leg to be matched to length variations in the measurement leg due to the shape of the part. This compensation is achieved by varying the length Lz over a quite large range, for example Lz=±250 mm for the testing of large aerospace parts.

On the other hand, the reference mirror (350) of the OCT system is moved over a small range of a few mm to measure the resin thickness. Thus, the mirror moving device (650) comprises, according to one particular embodiment, two actuators, each respectively ensuring the movement in one of the two ranges of variation of Lz.

Figure 7:
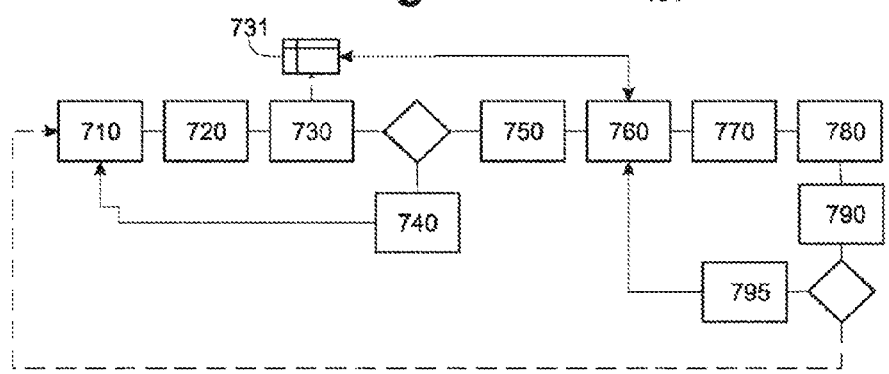
FIG. 7 is a flowchart of one example implementation of the method of the disclosure according to a first embodiment thereof.

Referring for example to FIG. 7, according to one example implementation of the first embodiment of the method of the disclosure, the latter comprises a step (710) comprising firing an OCT shot at the surface of the part. The result of this shot is analyzed in a step (720) comprising measuring the resin thickness in the location of the shot. The result of this thickness measurement is recorded in a table (731), in a recording step (730), with information allowing the position of the measurement on the surface of the part to be located. The measurement head is then moved (740) to another point and the thickness measurement cycle is repeated.

Once the entire surface to be tested has been scanned, the laser ultrasonic shot device is selected (750). An adjustment step (760) allows the parameters of the laser shot to be adjusted depending on the information in the table (731) relating to the surface resin thickness at the point targeted by the shot, so as to prevent the laser shot causing any degradation of the part. The shot is then fired (770), then analyzed (780) and the results are recorded (790). The laser head is then moved (795) to the following point and the above procedure is repeated starting from the adjustment step (760). Once the entire surface of the part has undergone ultrasonic testing, the thickness measurement may be repeated for all or some of the points so as to check that the part has not been degraded during the ultrasonic testing. Since the OCT device and the laser ultrasonic shot structure are arranged in the same measurement head and share the same scanner the surface of the part, the location on the surface of the laser ultrasonic shot is perfectly superposed on the location of the thickness measurement on the surface for each measurement point.

Figure 8:
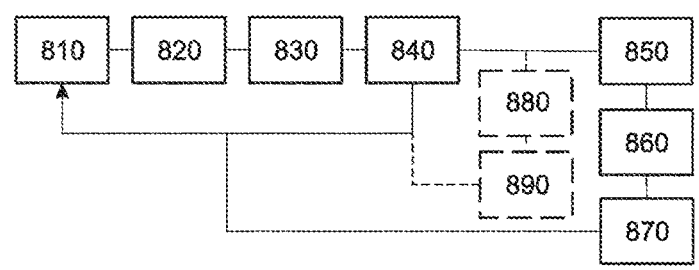
FIG. 8 is a flowchart of another example implementation of the method of the disclosure according to a second embodiment thereof.

Referring for example to FIG. 8, according to one example implementation of a second embodiment of the method of the disclosure, the latter comprises a first OCT shot (810), followed by a step (820) of analyzing this shot aiming to measure the resin thickness. Depending on the result of this measurement, the power of the laser ultrasonic shot is adjusted (830), and the laser ultrasonic shot is fired (840) with the power thus determined. The measurement head is then moved (850) to the following measurement point, in parallel the result of the laser ultrasonic shot is analyzed (860) and this result is recorded (870). The above steps are repeated until the part has been completely analyzed.

According to a variant of this embodiment, the recording step (870) also comprises recording the resin surface thickness measured in the preceding OCT shot analysis step (820). Thus, the method allows a map to be drawn of the material health of the part including local regions devoid of or poor in resin and zones corresponding to surplus resin, these variations in resin thickness also being quality flaws.

According to another variant of this second embodiment of the method of the disclosure, compatible with the preceding variants, the method comprises a step (880) in which an OCT shot is fired at the point hit by the preceding laser ultrasonic shot, then a step (890) of analysis of this OCT shot, in order to check that the laser ultrasonic shot has not caused degradation.

Figure 9:
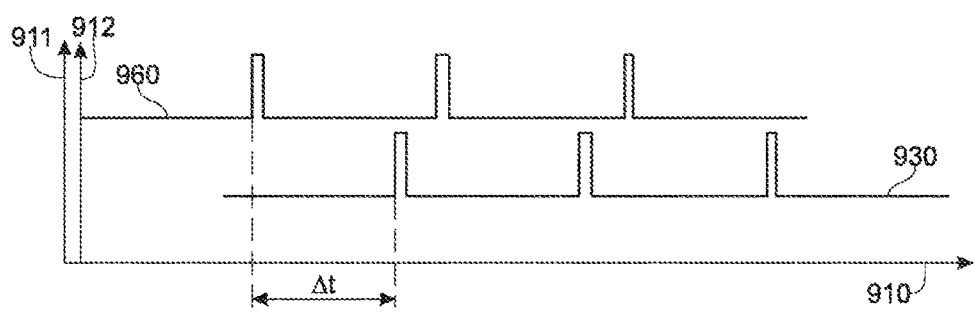
FIG. 9 illustrates a timing diagram showing the sequence of OCT laser pulses and laser ultrasonic shots applied to the surface of the part according to one example implementation of the second embodiment of the method of the disclosure.

Referring for example to FIG. 9, according to one example sequence as a function of time (910), the energy pulses (911) received by the part while the latter is being illuminated by the laser ultrasonic shot (930), and the energy pulses (912) received by the part while the latter is being illuminated by the OCT shot, are offset by a time Δt, the steps of analysis of the OCT shot and of adjustment of the power of the laser ultrasonic shot being carried out in this length of time Δt. Δt is about 10 ms ($10^{-2}$ seconds) for laser shot firing rates of 100 Hz. Thus, the time taken to test the part using this method, which combines surface resin thickness measurement and ultrasonic testing, is not significantly longer than the laser ultrasonic testing procedure known from the prior art, even though it is safer and provides additional test information.

While the methods and devices have been described herein in reference to specific embodiments, features, and illustrative embodiments, it will be appreciated that the utility of the subject matter is not thus limited, but rather extends to and encompasses numerous other variations, modifications and alternative embodiments, as will suggest themselves to those of ordinary skill in the field of the present subject matter, based on the disclosure herein.

Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims. It is understood that various details of the presently disclosed subject matter may be changed without departing from the scope of the presently disclosed subject matter. Furthermore, the foregoing description is for the purpose of illustration only, and not for the purpose of limitation.

While the disclosure herein has been described herein in reference to specific embodiments, features, and illustrative embodiments, it will be appreciated that the utility of the subject matter is not thus limited, but rather extends to and encompasses numerous other variations, modifications and alternative embodiments, as will suggest themselves to those of ordinary skill in the field of the present subject matter, based on the disclosure herein. Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims. It is understood that various details of the presently disclosed subject matter may be changed without departing from the scope of the presently disclosed subject matter. Furthermore, the foregoing description is for the purpose of illustration only, and not for the purpose of limitation.

The invention claimed is:

1. A method for nondestructive laser ultrasonic testing of a composite part containing fibrous reinforcements in a resin that optically scatters the laser light, the method comprising:
   measuring a thickness of the resin of the part in an area;
   adjusting a laser power setting of a laser configured to fire a laser ultrasonic shot at the area based on the measured thickness, including adjusting the laser power setting to reduce a risk of the fibrous reinforcements producing flashes while performing nondestructive testing of the area of the part;
   firing the laser ultrasonic shot at the area using the laser power setting; and
   analyzing a result of firing the laser ultrasonic shot at the area, thereby nondestructively testing the area of the part.

2. The method of claim 1, wherein measuring the thickness comprises using an optical coherence tomography (abbreviated OCT) technique.

3. The method of claim 1, wherein adjusting the laser power setting comprises modifying the focus of the laser.

4. The method of claim 1, wherein adjusting the laser power setting comprises modifying the power of the laser radiation of the ultrasonic shot.

5. The method of claim 1, wherein measuring the thickness of the resin comprises:
   taking a series of thickness measurements over an entire area of the part; and
   recording the thickness values measured in a table containing for each thickness value a spatial location of the measurement point.

6. The method of claim 5, comprising adjusting the laser power setting and firing a laser ultrasonic shot for each measurement of the series of measurements, thereby testing the entire area of the part.

7. A system for nondestructive laser ultrasonic testing of a composite part containing fibrous reinforcements in a resin that optically scatters the laser light, comprising:
   a first laser source configured to produce laser ultrasonic shots;
   an OCT device comprising a second laser source and an interferometer, the interferometer comprising a scanning mirror located in a measurement path of length LM configured to project laser radiation from the first and second laser sources onto the part;
   an optical fiber of length Lf located in a reference path and a reference mirror placed at a distance Lz from an exit of the optical fiber such that LM=Lf+Lz; and
   an information-processing device configured to cause the system to perform operations comprising:
      measuring, using the second laser, a thickness of the resin of the part in an area;
      adjusting a laser power setting for the first laser based on the measured thickness, including adjusting the laser power setting to reduce a risk of the fibrous reinforcements producing flashes while performing nondestructive testing of the area of the part;
      firing, using the first laser, a laser ultrasonic shot at the area using the laser power setting; and analyzing a result of firing the laser ultrasonic shot at the area, thereby nondestructively testing the area of the part.

8. The system of claim 7, comprising:
a motorized displacement stage holding the reference mirror so that the distance Lz may be varied.

9. The system of claim 7, wherein the information-processing device is configured to adjust the laser power setting for the first laser in a time shorter than or equal to a time $\Delta t$ separating shots from the first laser source and the second laser source.

10. The system of claim 9, wherein $\Delta t$ is shorter than or equal to 10 ms.

* * * * *